US011925509B2

(12) United States Patent
Adachi et al.

(10) Patent No.: US 11,925,509 B2
(45) Date of Patent: Mar. 12, 2024

(54) ULTRASONIC PROBE, ULTRASONIC DIAGNOSTIC SYSTEM, METHOD OF CONTROLLING ULTRASONIC PROBE, AND NON- TRANSITORY COMPUTER-READABLE RECORDING MEDIUM

(71) Applicant: SOCIONEXT INC., Kanagawa (JP)

(72) Inventors: Naoto Adachi, Yokohama (JP); Hiroaki Takagi, Yokohama (JP)

(73) Assignee: SOCIONEXT INC., Kanagawa (JP)

( * ) Notice: Subject to any disclaimer, the term of this patent is extended or adjusted under 35 U.S.C. 154(b) by 121 days.

(21) Appl. No.: 17/560,113

(22) Filed: Dec. 22, 2021

(65) Prior Publication Data
US 2022/0110611 A1  Apr. 14, 2022

Related U.S. Application Data

(63) Continuation of application No. PCT/JP2019/026808, filed on Jul. 5, 2019.

(51) Int. Cl.
A61B 8/00 (2006.01)
(52) U.S. Cl.
CPC .......... *A61B 8/546* (2013.01); *A61B 8/4472* (2013.01)
(58) Field of Classification Search
CPC ................ A61B 8/546; A61B 8/4472
See application file for complete search history.

(56) References Cited

U.S. PATENT DOCUMENTS

2012/0226160 A1  9/2012 Kudoh
2015/0164483 A1  6/2015 Miyajima et al.
(Continued)

FOREIGN PATENT DOCUMENTS

CN  104602612 A  5/2015
JP  2005-253776 A  9/2005
(Continued)

OTHER PUBLICATIONS

Chinese Office Action dated Apr. 13, 2023 issued in corresponding Chinese Patent Application No. 201980098005.3, w/English translation.
(Continued)

*Primary Examiner* — Dixomara Vargas
(74) *Attorney, Agent, or Firm* — Rimon, P.C.

(57) ABSTRACT

An ultrasonic probe includes a transducer; a pulser; an amplifier; a wireless transmitter; temperature detectors at two or more locations from among a location of the pulser, a location of the amplifier, and a location of the wireless transmitter; and a processor comparing temperatures detected by the temperature detectors with first temperature thresholds set for the temperature detectors, and, when one or more temperature detectors detect temperatures that exceed corresponding first temperature thresholds, selecting any one of low power consumption operating modes based on which temperature detectors are the one or more temperature detectors detecting the temperatures that exceed corresponding first temperature thresholds, and switching an operating mode of each of one or more from among the pulser, the amplifier, and the wireless transmitter from a normal operating mode to the selected low power consumption operating mode.

11 Claims, 14 Drawing Sheets

(56) References Cited

U.S. PATENT DOCUMENTS

| | | |
|---|---|---|
| 2018/0153510 A1 | 6/2018 | Haque et al. |
| 2018/0242956 A1* | 8/2018 | Somerville ............ A61B 8/488 |
| 2019/0175149 A1* | 6/2019 | Dickie ................. A61B 8/4254 |
| 2021/0022706 A1* | 1/2021 | Haque .................. B06B 1/0692 |
| 2021/0124044 A1* | 4/2021 | Haque .................... A61B 8/488 |
| 2021/0293952 A1* | 9/2021 | Haque ................. G10K 11/343 |
| 2022/0233168 A1* | 7/2022 | Haque .................. B06B 1/0215 |

FOREIGN PATENT DOCUMENTS

| | | |
|---|---|---|
| JP | 2012-011118 A | 1/2012 |
| JP | 2012-179328 A | 9/2012 |
| JP | 2012-228425 A | 11/2012 |
| JP | 2019-017759 A | 2/2019 |

OTHER PUBLICATIONS

International Search Report issued in corresponding International Patent Application No. PCT/JP2019/026808 dated Sep. 17, 2019, with English translation.

\* cited by examiner

ULTRASONIC PROBE, ULTRASONIC DIAGNOSTIC SYSTEM, METHOD OF CONTROLLING ULTRASONIC PROBE, AND NON-TRANSITORY COMPUTER-READABLE RECORDING MEDIUM

CROSS-REFERENCE TO RELATED APPLICATION

The present application is a continuation of International application No. PCT/JP2019/026808 filed on Jul. 5, 2019 and designated the U.S., the entire contents of which are incorporated herein by reference.

BACKGROUND OF THE INVENTION

1. Field of the Invention

The present invention relates to an ultrasonic probe, an ultrasonic diagnostic system, a method of controlling an ultrasonic probe, and a non-transitory computer-readable recording medium.

2. Description of the Related Art

An ultrasonic diagnostic system, which includes an ultrasonic probe, outputting an ultrasonic wave to a subject and receiving an ultrasonic wave reflected by the subject, and produces an ultrasonic image from the reflected ultrasonic wave, is known. For example, an ultrasonic probe adjusts a drive voltage, a transmission numerical aperture, a transmission frequency, a frame rate, and the like according to a temperature detected by a temperature sensor provided at an ultrasonic-wave transmission/reception unit so as to control a surface temperature of the ultrasonic-wave transmission/reception unit that contacts the subject such that the surface temperature is lower than or equal to a predetermined temperature.

Recently, an ultrasonic diagnostic system has become more compact and wireless, with a plurality of heat generating components incorporated into an ultrasonic probe. In this type of an ultrasonic diagnostic system, a plurality of temperature sensors for measuring temperatures of the plurality of heat generating components are built into the ultrasonic probe, and, when a surface temperature of the ultrasonic probe rises, the ultrasonic diagnosis system is switched from a high image quality mode to a low image quality mode. A duration of the high image quality mode is calculated based on a temperature measured by a temperature sensor, and is displayed on a screen.

Patent Document 1: Japanese Patent Application Publication No. 2005-253776
Patent Document 2: Japanese Patent Application Publication No. 2012-179328

SUMMARY

In one aspect of an embodiment, an ultrasonic probe includes a transducer configured to transmit an ultrasonic wave to a subject and output an ultrasonic wave reflected by the subject as a signal; a pulser configured to generate a pulse to be output to the transducer; an amplifier configured to amplify the signal; a wireless transmitter configured to transmit data obtained from a signal that has been amplified by the amplifier to outside; a plurality of temperature detectors at two or more locations from among a location of the pulser, a location of the amplifier, and a location of the wireless transmitter; and a processor configured to compare temperatures detected by the respective temperature detectors with first temperature thresholds set for the respective temperature detectors, the processor being further configured to, when one or more of the plurality of temperature detectors detect temperatures that exceed corresponding ones of the first temperature thresholds, select any one of a plurality of low power consumption operating modes based on which ones of the plurality of temperature detectors are the one or more of the plurality of temperature detectors detecting the temperatures that exceed the corresponding ones of the first temperature thresholds, and the processor being further configured to switch an operating mode of each of one or more from among the pulser, the amplifier, and the wireless transmitter from a normal operating mode to the one of the plurality of low power consumption operating modes selected by the processor.

The object and advantages of the invention will be implemented and attained by the elements and combinations particularly pointed out in the appended claims.

It is to be understood that both the foregoing overall description and the following detailed description are exemplary and explanatory and are not restrictive of the invention as claimed.

BRIEF DESCRIPTION OF DRAWINGS

Other objects and further features of embodiments will become apparent from the following detailed description when read in conjunction with the accompanying drawings, in which:

FIG. 2 depicts an example of an external shape of the ultrasonic probe depicted in FIG. 1, and an example of positions of heat generating components and the like;

DESCRIPTION OF EMBODIMENT

In the related art described above, as the number of components built into the ultrasonic probe increases, an amount of heat generation in the ultrasonic probe tends to increase and a surface temperature of the ultrasonic probe tends to increase. Preferably, the surface temperature of the ultrasonic probe is such that an operator holding and operating the ultrasonic probe does not feel hot. Temperatures at various locations on the surface of the ultrasonic probe differ from each other depending on locations of heat generating components located within the ultrasonic probe. Therefore, it is preferable that, while operations of the ultrasonic probe are continued, the amounts of heat generation in the heat generating components are adjusted so that the operator operates the ultrasonic probe without feeling hot.

In view of the above-described points, embodiments will be described below for a purpose of setting a surface temperature of an ultrasonic probe to a desired temperature.

Hereinafter, the embodiments will be described with reference to the drawings.

First Embodiment

Figure 1:
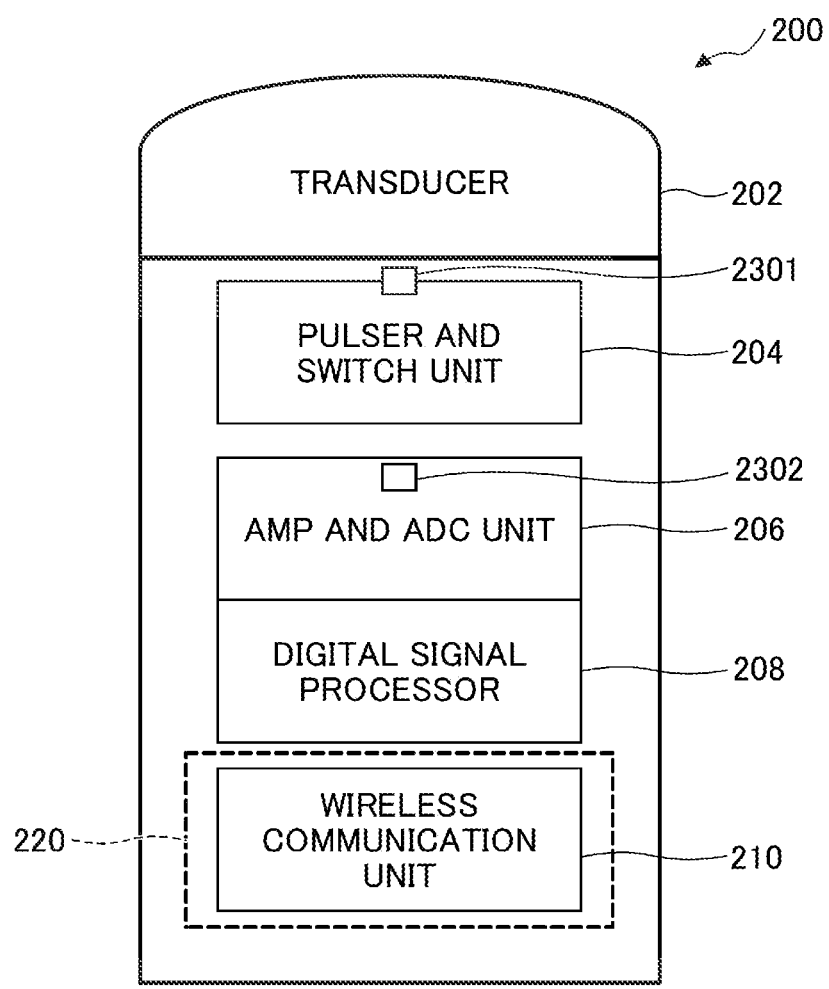
FIG. 1 is a diagram depicting an overall configuration of an ultrasonic probe according to a first embodiment.

FIG. 1 depicts an overall configuration of an ultrasonic probe 200 according to a first embodiment. FIG. 1 depicts positional relationships of various components in the ultrasonic probe 200, and does not depict sizes of the various components.

The ultrasonic probe 200 includes a transducer 202, a pulser and switch unit 204, an amplifier (AMP) and analog to digital converter (ADC) unit 206, a digital signal processor 208, a wireless communication unit 210, a battery 220, and a plurality of temperature sensors 230 (i.e., temperature sensors 2301 and 2302). The ultrasonic probe 200 outputs ultrasonic waves to a subject not depicted, receives reflected waves (ultrasonic waves) reflected by the subject, and generates ultrasonic image data based on the received reflected waves.

Alternatively, thermistors may be used in place of the respective temperature sensors 2301 and 2302. The temperature sensors 2301 and 2302 and the thermistors are examples of temperature detectors. Hereinafter, the temperature sensors 2301 and 2302 are also referred to as the temperature sensors 230 when they are described without distinguishing therebetween.

The temperature sensor 2301 is set near the transducer 202 and near the pulser and switch unit 204 to detect an ambient temperature of the transducer 202 and the pulser and switch unit 204. The temperature sensor 2301 may be set in contact with one of the transducer 202 and the pulser and switch unit 204, and may be set between the transducer 202 and the pulser and switch unit 204.

The temperature sensor 2302 is set near or in contact with an amplifier of the AMP and ADC unit 206 to detect an ambient temperature of the amplifier. The battery 220 supplies power to heat generating components such as the transducer 202, the pulser and switch unit 204, the AMP and ADC unit 206, the digital signal processor 208, and the wireless communication unit 210. The transducer 202, the pulser and switch unit 204, the AMP and ADC unit 206, the digital signal processor 208, and the wireless communication unit 210 will be described with reference to FIG. 3. The ultrasonic probe 200 may be driven by an external power source, and, in this case, the ultrasonic probe does not include the battery 220. In addition, when the ultrasonic probe 200 communicates with outside through wired communication, a wired communication unit is provided in place of the wireless communication unit 210.

Figure 2:
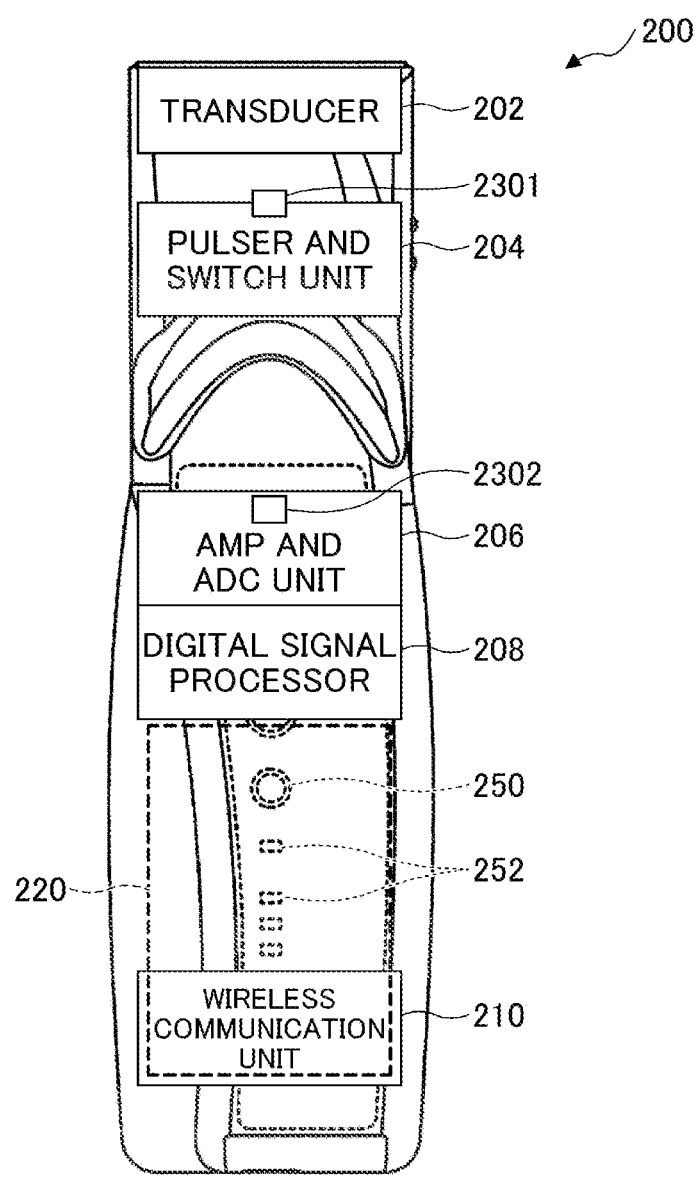

FIG. 2 depicts an example of an external shape of the ultrasonic probe 200 of FIG. 1, and an example of positions of the heat generating components and the like. The ultrasonic probe 200 has an elongated shape when viewed from a side where an operation button 250, light emitting diodes (LEDs) 252, and the like are provided. For example, the transducer 202 and the pulser and switch unit 204 are provided in this order from a tip of the ultrasonic probe 200 at an upper side of FIG. 2, and the temperature sensor 2301 is provided on the transducer 202 side of the pulser and switch unit 204. The tip of the ultrasonic probe 200, at which the transducer 202 is exposed, comes into contact with a subject.

The AMP and ADC unit 206 and the digital signal processor 208 are provided substantially in the middle with respect to a length of the ultrasonic probe 200, and the temperature sensor 2302 is provided on the pulser and switch unit 204 unit side of the AMP and ADC unit 206. The wireless communication unit 210 is provided at a rear end side (opposite to the tip side) of the ultrasonic probe 200 located at a lower side in FIG. 2.

For example, the transducer 202, the pulser and switch unit 204, the AMP and ADC unit 206, the digital signal processor 208, and the wireless communication unit 210 are provided at a front side in a casing of the ultrasonic probe 200. The battery 220 is provided at a back side in the casing and extends from the center to the rear end side of the ultrasonic probe 200.

Figure 3:
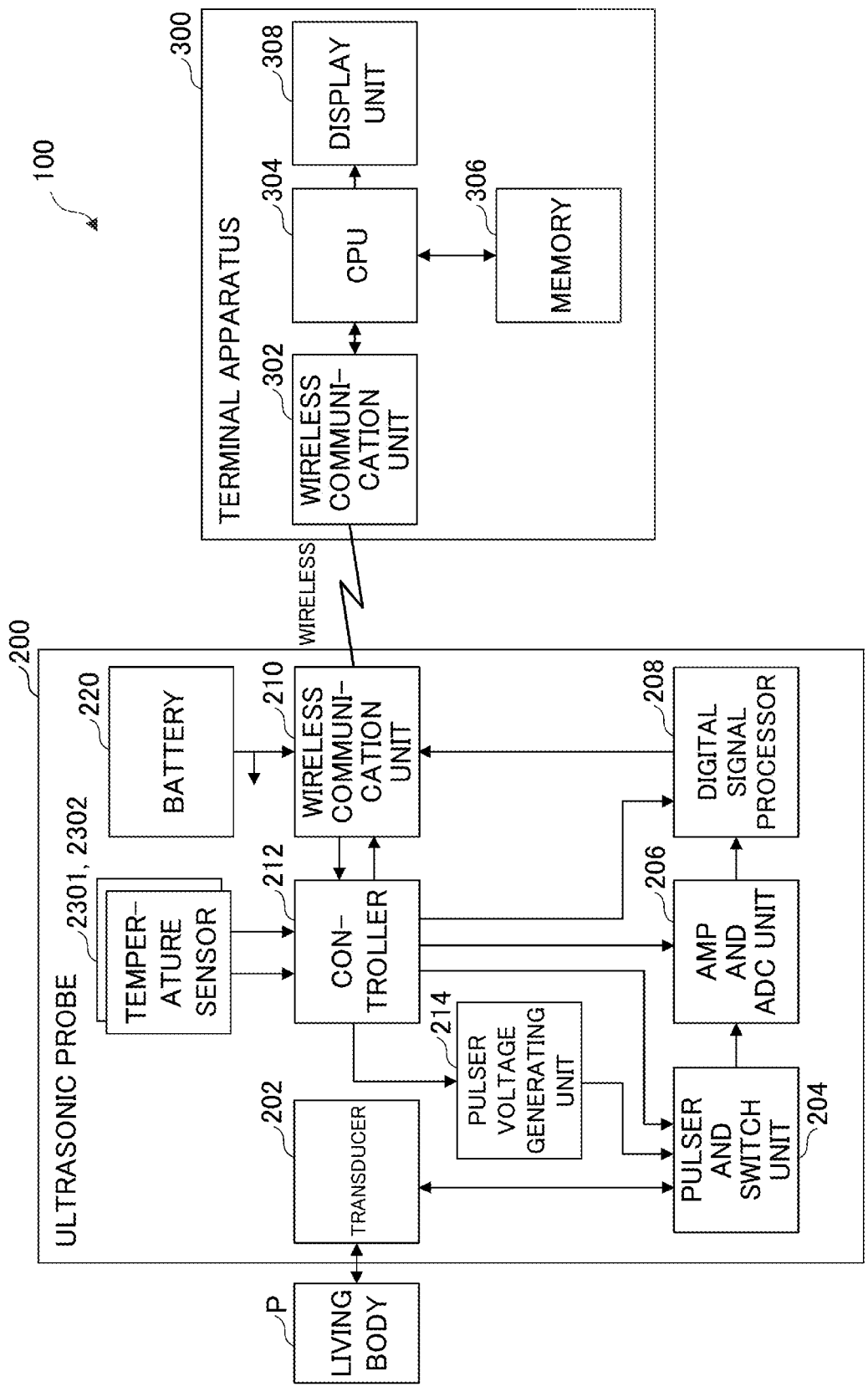
FIG. 3 is a diagram depicting an example of a configuration of an ultrasonic diagnostic system according to the first embodiment.

FIG. 3 depicts an example of a configuration of an ultrasonic diagnostic system 100 according to the first embodiment. The ultrasonic diagnostic system 100 depicted in FIG. 3 includes the ultrasonic probe 200 depicted in FIG. 1 and a terminal apparatus 300. The ultrasonic probe 200 and the terminal apparatus 300 communicate wirelessly with each other. For example, the terminal apparatus 300 may be a general purpose terminal, such as a tablet terminal.

The ultrasonic probe 200 includes a controller 212 and a pulser voltage generating unit 214 in addition to the elements depicted in FIG. 1. The terminal apparatus 300 includes a wireless communication unit 302, a central processing unit (CPU) 304, a memory 306, and a display unit 308.

The transducer 202 includes an oscillator array (not depicted) arranged in a form of an array at a position facing a living body P (i.e., a subject) and outputs ultrasonic waves generated by the transducer array based on pulse signals generated by the pulser and switch unit 204 to the living body P. Ultrasonic waves entering the living body P are reflected at boundaries with respect to different acoustic impedances. The transducer 202 receives ultrasonic waves (reflected waves) reflected from the living body P and outputs the received ultrasonic waves as signals to the pulser and switch unit 204.

The pulser and switch unit 204 selects the transducer 202 through switches and transmits pulse signals from pulsers to the transducer 202 to cause the transducer 202 to output ultrasonic waves. The pulser and switch unit 204 receives signals that are generated by the transducer 202 based on reflected waves, and outputs the received signals to the amplifier of the AMP and ADC unit 206 selected through the switches.

The AMP and ADC unit 206 amplifies the signals representing the reflected ultrasonic waves received from the pulser and switch unit 204 through the amplifier, converts the signals to digital signals through an ADC, and outputs the digital signals to the digital signal processor 208. For example, the AMP and ADC unit 206 includes the amplifier having 32 channels, and the number of channels indicated by the controller 212 are operated from among the 32 channels. Although power consumption of the AMP and ADC unit 206 increases as the channels in operation increase in number, image quality of ultrasonic image data generated by the digital signal processor 208 increases because of an increase in the amount of data. In contrast, as the channels in operation decrease in number, power consumption of the AMP and ADC unit 206 decreases. However, because the amount of data decreases, image quality of ultrasonic image data generated by the digital signal processor 208 decreases.

The digital signal processor 208 performs various processes on digital signals received from the AMP and ADC unit 206 to generate ultrasonic image data and outputs the generated ultrasonic image data to the wireless communication unit 210. For example, the digital signal processor 208 performs a process of making coincident the timings, of signals representing reflected waves output from the pulser and switch unit 204, an averaging process (a phasing and summing process) on the signals, a gain correcting process on the signals taking into consideration attenuation of the reflected waves in the living body P, and envelope processing on the signals for obtaining brightness information. The digital signal processor 208 transmits ultrasonic image data to the wireless communication unit 210 using, for example, a serial peripheral interface (SPI).

The wireless communication unit 210 performs wireless communication in accordance with a standard such as Wi-Fi (registered trademark) with the wireless communication unit 302 of the terminal apparatus 300 that is an external apparatus with respect to the ultrasonic probe 200. Wireless communication between the wireless communication units 210 and 302 is not limited to communication in accordance with Wi-Fi, and another standard may be used instead. The wireless communication unit 210 outputs an ultrasonic wave emission instruction or the like received from the terminal apparatus 300 to the controller 212 using, for example, an I-squared-C (I²C) interface. The wireless communication unit 210 transmits ultrasonic image data received from the digital signal processor 208 to the wireless communication unit 302 of the terminal apparatus 300. Ultrasonic image data transmitted from the ultrasonic probe 200 to the terminal apparatus 300 is a digital signal (digital data).

For example, in the wireless communication unit 210, a frame rate of ultrasonic image data to be transmitted to the wireless communication unit 302 of the terminal apparatus 300 is changeable, based on an instruction from the controller 212. As a frame rate increases, greater power consumption of the wireless communication unit 210 is required, but a change in an image displayed on the display unit 308 of the terminal apparatus 300 is implemented in a smoother manner. In contrast, as a frame rate decreases, smaller power consumption of the wireless communication unit 210 is required, but a change in an image displayed on the display unit 308 of the terminal apparatus 300 is implemented in a less smooth manner. When a frame rate is to be lowered, for example, the oscillators in operation in the transducer 202 are reduced in number, the pulsers in operation are reduced in number and the switches in operation are reduced in number in the pulser and switch unit 204, and the channels of the AMP and ADC unit in operation 206 are reduced in number, concurrently with the lowering of the frame rate.

The battery 220 is chargeable, for example, via a power supply terminal (not depicted), and provides power to the elements of the ultrasonic probe 200. Each of the temperature sensors 2301 and 2302 outputs temperature information representing a measured temperature to the controller 212. The ultrasonic probe 200 may include three or more temperature sensors 230. Each temperature sensor 230 is preferably provided in contact with or near a heat generating component that generates a relatively high amount of heat.

The controller 212 controls the whole ultrasonic probe 200. For example, functions of the controller 212 are implemented as a result of a control program being executed by a processor such as a CPU which controls operations of the ultrasonic probe 200. For example, the controller 212 controls the pulser and switch unit 204 to output ultrasonic waves to the transducer 202 in response to a measurement start instruction received from the terminal apparatus 300 via the wireless communication unit 210. The controller 212 causes the digital signal processor 208 to generate ultrasonic image data of an image representing reflected waves reflected by the living body P.

The controller 212 stops operations of the pulser and switch unit 204, the digital signal processor 208, and the like in response to a measurement stop instruction received from the terminal apparatus 300 via the wireless communication unit 210. A measurement start instruction and a measurement stop instruction may be generated in response to operating of the operation button 250 (FIG. 2) by an operator provided on the front side of the casing of the ultrasonic probe 200.

The controller 212 controls power consumption of the pulser and switch unit 204 or the AMP and ADC unit 206, or both of these units based on a temperature measured by each temperature sensor 230. As a result, it is possible to adjust an amount of heat generation in either one or both of the pulser and switch unit 204 and the AMP and ADC unit 206 so that a surface temperature of the casing of the ultrasonic probe 200 can be set to a temperature such that an operator holding the ultrasonic probe 200 does not feel hot. A temperature at the tip of the transducer 202 can also be set to a temperature such that a subject does not feel hot. The control of power consumption by the controller 212 will be described with reference to FIGS. 4 and 5.

The pulser voltage generating unit 214 generates drive voltages for the pulsers of the pulser and switch unit 204 under the control of the controller 212. The drive voltages for the pulsers can be adjusted under the control of the controller 212.

The wireless communication unit 302 of the terminal apparatus 300 receives ultrasonic image data and the like from the wireless communication unit 210 of the ultrasonic probe 200. The wireless communication unit 302 transmits an ultrasonic wave emission instruction and the like to the wireless communication unit 210 of the ultrasonic probe 200. The CPU 304 controls overall operation of the terminal apparatus 300, for example, by executing a program. The memory 306 stores ultrasonic image data received by the wireless communication unit 302, various programs executed by the CPU 304, and data used by the various programs.

The display unit 308 displays an ultrasonic image or the like received from the ultrasonic probe 200. An ultrasonic image displayed on the display unit 308 may be a moving image obtained during scanning of the living body P by the ultrasonic probe 200 and may be a still image obtained when scanning of the living body P by the ultrasonic probe 200 is stopped. When the terminal apparatus 300 is a general purpose terminal such as a tablet terminal, the display unit 308 may include a touch panel.

Figure 4:
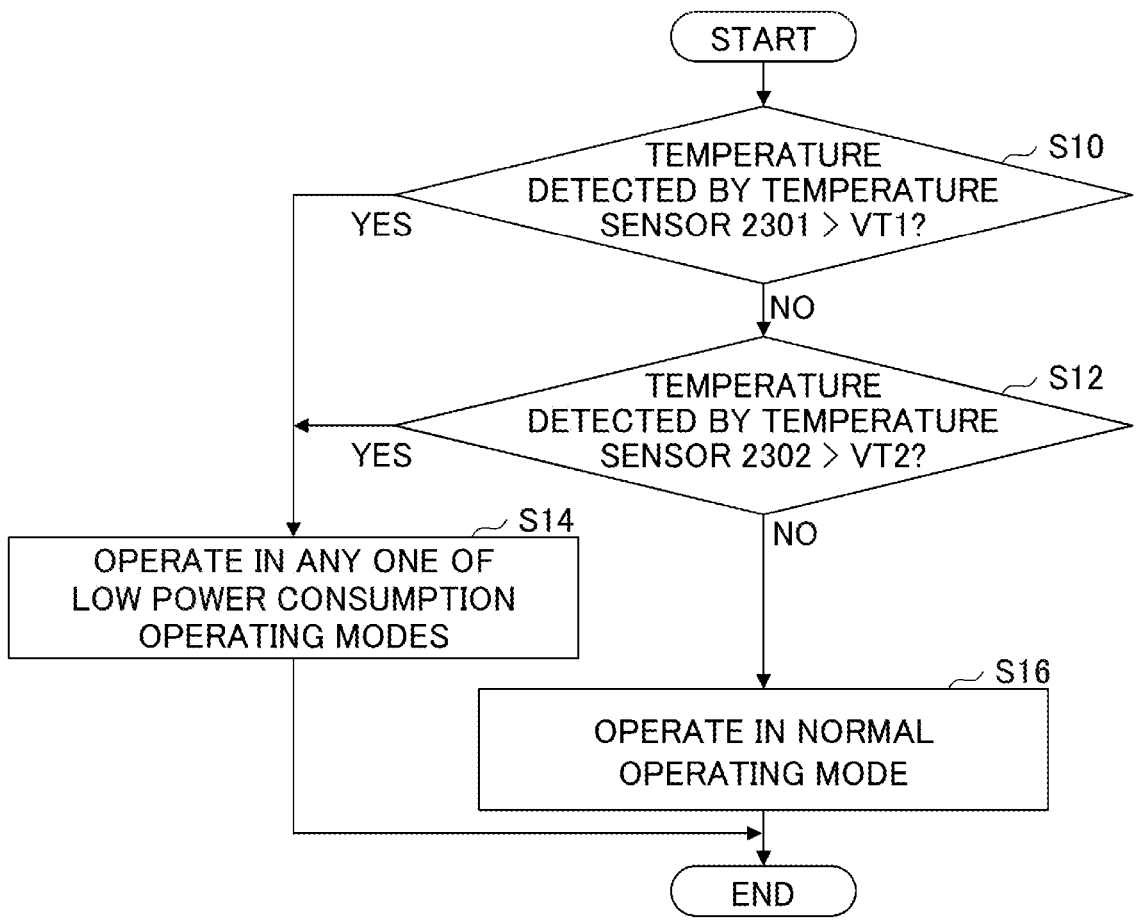
FIG. 4 is a diagram depicting an example of operations of the ultrasonic probe depicted in FIG. 3.

FIG. 4 depicts an example of operations of the ultrasonic probe 200 of FIG. 3. For example, an operation flow depicted in FIG. 4 is implemented by a control program executed by the controller 212 (i.e., the CPU) of FIG. 3. That is, FIG. 4 depicts an example of a method of controlling the ultrasonic probe 200 and an example of a control program for implementing the method. The operation flow depicted in FIG. 4 is repeated at a predetermined period (e.g., every second or every 100 milliseconds).

First, in step S10, the controller 212 compares a temperature detected by the temperature sensor 2301 near the transducer 202 and near the pulser and switch unit 204 with a temperature threshold VT1. The controller 212 determines whether the temperature detected by the temperature sensor 2301 exceeds the temperature threshold VT1. When the temperature detected by the temperature sensor 2301 exceeds the temperature threshold VT1, the controller 212 performs step S14, and when the temperature detected by the temperature sensor 2301 is lower than or equal to the temperature threshold VT1, the controller 212 performs step S12.

In step S12, the controller 212 compares a temperature detected by the temperature sensor 2302 near the AMP and ADC unit 206 with a temperature threshold VT2. The controller 212 determines whether the temperature detected by the temperature sensor 2302 exceeds the temperature threshold VT2. When the temperature detected by the temperature sensor 2302 exceeds the temperature threshold VT2, the controller 212 performs step S14, and when the temperature detected by the temperature sensor 2302 is lower than or equal to the temperature threshold VT2, the controller 212 performs step S16. The temperature thresholds VT1 and VT2 are examples of first temperature thresholds. For example, the temperature thresholds VT1 and VT2 may be set to the same value.

In step S14, the controller 212 switches an operating mode of the ultrasonic probe 200 to any one of a plurality of low power consumption operating modes because either one of the temperatures measured by the two temperature sensors 230 exceeds a temperature threshold set for the corresponding one of the temperature sensors 230. In step S16, the controller 212 maintains an operating mode or switches an operating mode of the ultrasonic probe 200 to a normal operating mode.

The temperature threshold VT1 may be set such that the temperature threshold VT1 is lower than the temperature threshold VT2. As a result, it is possible to cause a temperature at the tip of the transducer 202 in direct contact with a subject's skin to be lower than the maximum temperature of the casing of the ultrasonic probe 200 held by an operator of the ultrasonic probe 200, as will be described with reference to FIG. 5. Therefore, the subject can be prevented from feeling discomfort.

The subject is a patient or the like whose ultrasonic images are taken by the ultrasonic probe 200. Although not particularly limited, it is preferable that each of a temperature at the tip of the transducer 202 and a surface temperature of the casing of the ultrasonic probe 200 be lower than or equal to a temperature (e.g., 40° C.) that does not cause a low temperature burn injury.

Note that, in the ultrasonic probe 200, amounts of heat generation in the pulser and switch unit 204 and the AMP and ADC unit 206 are greatest, and temperatures are maximum at positions on the casing facing the pulser and switch unit 204 and the AMP and ADC unit 206. Various components are densely mounted in the casing of the ultrasonic probe 200, and there is little clearance between the inner surface of the casing and the various components. Therefore, a surface temperature of the casing is approximately the same as a temperature detected by a corresponding one of the temperature sensors 230.

Figure 5:
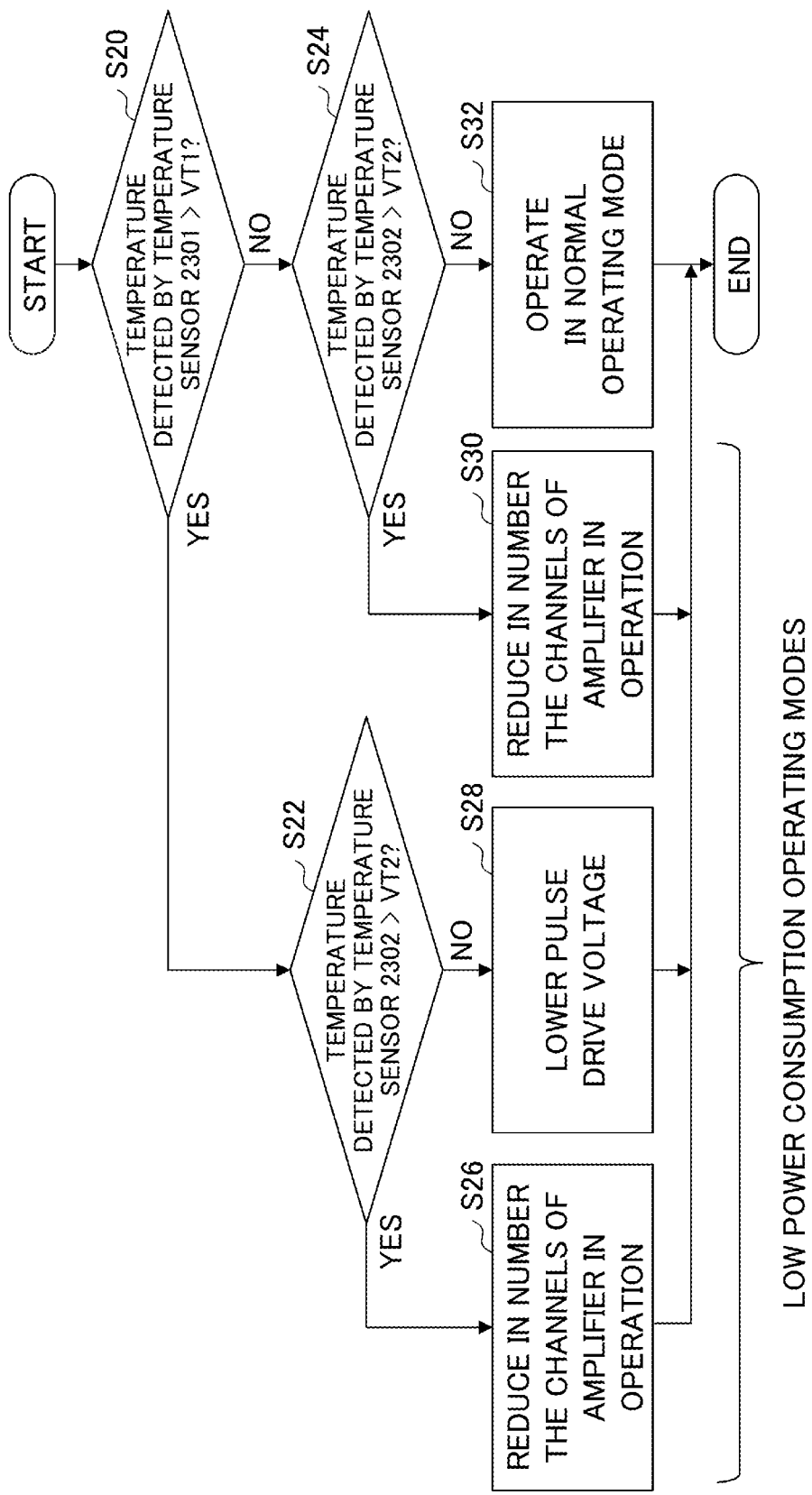
FIG. 5 is a diagram depicting a specific example of operations depicted in FIG. 4.

FIG. 5 depicts a specific example of operations depicted in FIG. 4. A determination of step S20 is the same as a determination of step S10 of FIG. 4, and each of determinations of steps S22 and S24 is the same as a determination of step S12 of FIG. 4.

In step S20, when a temperature measured by the temperature sensor 2301 exceeds the temperature threshold VT1, the controller 212 performs step S22, and when the temperature measured by the temperature sensor 2301 is lower than or equal to the temperature threshold VT1, the controller 212 performs step S24.

In step S22, when a temperature measured by the temperature sensor 2302 exceeds the temperature threshold VT2, the controller 212 performs step S26, and when the temperature measured by the temperature sensor 2302 is lower than or equal to the temperature threshold VT2, the controller 212 performs step S28.

In step S24, when the temperature measured by the temperature sensor 2302 exceeds the temperature threshold VT2, the controller 212 performs step S30, and when the temperature measured by the temperature sensor 2302 is lower than or equal to the temperature threshold VT2, the controller 212 performs step S32.

In each of steps S26 and S30, the controller 212 reduces in number the channels of the amplifier in operation. For example, in a low power consumption operating mode, the controller 212 reduces in number the channels in operation from 32 in the normal operating mode to 24, 16, or the like. When the temperature measured by the temperature sensor 2302 exceeds the temperature threshold VT2, the controller 212 reduces in number the channels of the amplifier in operation regardless of the temperature measured by the temperature sensor 2301.

The controller 212 also reduces in number the pulsers in operation and reduce in number the switches in operation in the pulser and switch unit 204 in response to a reduction in number of the channels of the amplifier in operation. This reduces not only an amount of heat generation in the amplifier but also an amount of heat generation in the pulser and switch unit 204. Therefore, by repeating a process of FIG. 5, an ambient temperature of the AMP and ADC unit 206 can be kept to be lower than or equal to the temperature threshold VT2, and the ambient temperature of the pulser and switch unit 204 can be kept to be lower than or equal to the temperature threshold VT1. For example, also a temperature at the tip of the transducer 202 may be kept to be lower than or equal to the temperature threshold VT1. Thus, it is possible to prevent both a subject and an operator who holds and operates the ultrasonic probe 200 from feeling discomfort.

In a case where an ambient temperature of the AMP and ADC unit 206 does become lower than or equal to the temperature threshold VT2 even as a result of a flow of FIG. 5 being repeated a plurality of times, the channels of the amplifier in operation may be gradually reduced in number to, for example, 24, 16, and, then, 8. Concurrently with the reduction in number of the channels of the amplifier in operation, also the pulsers in operation are reduced in number and the switches in operation are reduced in number in the pulser and switch unit 204.

In step S28, the controller 212 controls the pulser voltage generating unit 214 to reduce drive voltages for the pulsers of the pulser and switch unit 204. For example, in a low power consumption operating mode, the controller 212 reduces drive voltages for the pulsers from 50 V in the normal operating mode to 40 V, 30 V, 20 V, or the like. By thus lowering drive voltages for the pulsers, intensity of reflected waves decreases, thereby reducing brightness of an ultrasonic image (data) generated by the digital signal processor 208. However, in step S28, because the channels of the amplifier in operation are not reduced in number, degradation in image quality of the ultrasonic image can be prevented.

In step S28, as a result of the reduction in the drive voltages for the pulsers, power consumption of the pulser and switch unit 204 can be reduced, and also, an amount of heat generation in the pulser and switch unit 204 can be reduced. As a result, it is possible to lower a temperature of the pulser and switch unit 204. Also a drive voltage for the transducer 202 is reduced accordingly, and, as a result, it is possible to lower a temperature of the transducer 202.

Therefore, by repeating a process of FIG. 5, ambient temperatures of the pulser and switch unit 204 and the transducer 202 can be kept to be lower than or equal to the temperature threshold VT1, thereby preventing a subject from feeling discomfort. In a case where an ambient temperature of the pulser and switch unit 204 does not become lower than or equal to the temperature threshold VT1 even as a result of a flow of FIG. 5 being performed a plurality of times, drive voltages for the pulsers may be gradually reduced to, for example, 40V, 30V, and, then, 20V.

In step S32, the controller 212 causes the ultrasonic probe 200 to operate in the normal operating mode and controls an operation of a circuit of each element of the ultrasonic probe 200 according to the normal operating mode. For example, in the normal operating mode, the number of channels of the amplifier in operation is 32, drive voltages for the pulsers is 50 V, and a frame rate of ultrasonic image data generated by the digital signal processor 208 is 20 frames per second (fps).

As depicted in FIG. 5, two types of low power consumption operating modes are used, i.e., a low power consumption operating mode of changing in number the channels of the amplifier in operation and a low power consumption operating mode of changing drive voltages for the pulsers. As described above, in each low power consumption operating mode, the channels of the amplifier in operation may be sequentially decreased in number, and the drive voltages for the pulsers may be gradually decreased. That is, power consumption may be finely adjusted in each low power consumption operating mode.

As described above, according to the first embodiment, power consumption of a component near the temperature sensor 230 that detects a temperature exceeding the temperature threshold VT1 (or VT2) can be reduced, thereby reducing an amount of heat generation. For example, by reducing in number the channels of the amplifier in operation, an amount of heat generation in the AMP and ADC unit 206 can be reduced, and by lowering drive voltages for the pulsers, an amount of heat generation in the pulser and switch unit 204 can be reduced.

As a result, it is possible to cause a surface temperature of the casing of the ultrasonic probe 200 at a position that differs depending on a position of a heat generating component to be lower than or equal to the temperature threshold VT1 (or VT2). That is, a surface temperature of the casing of the ultrasonic probe 200 can be set to a desired temperature, without depending on each of the specific positions of the heat generating components. This prevents both a subject and an operator of the ultrasonic probe 200 from feeling discomfort.

By setting the temperature threshold VT1 to be lower than the temperature threshold VT2, it is possible to cause a temperature at the tip of the transducer 202 to be lower than a surface temperature of the casing of the ultrasonic probe 200, further preventing a subject from feeling discomfort.

Second Embodiment

Figure 6:
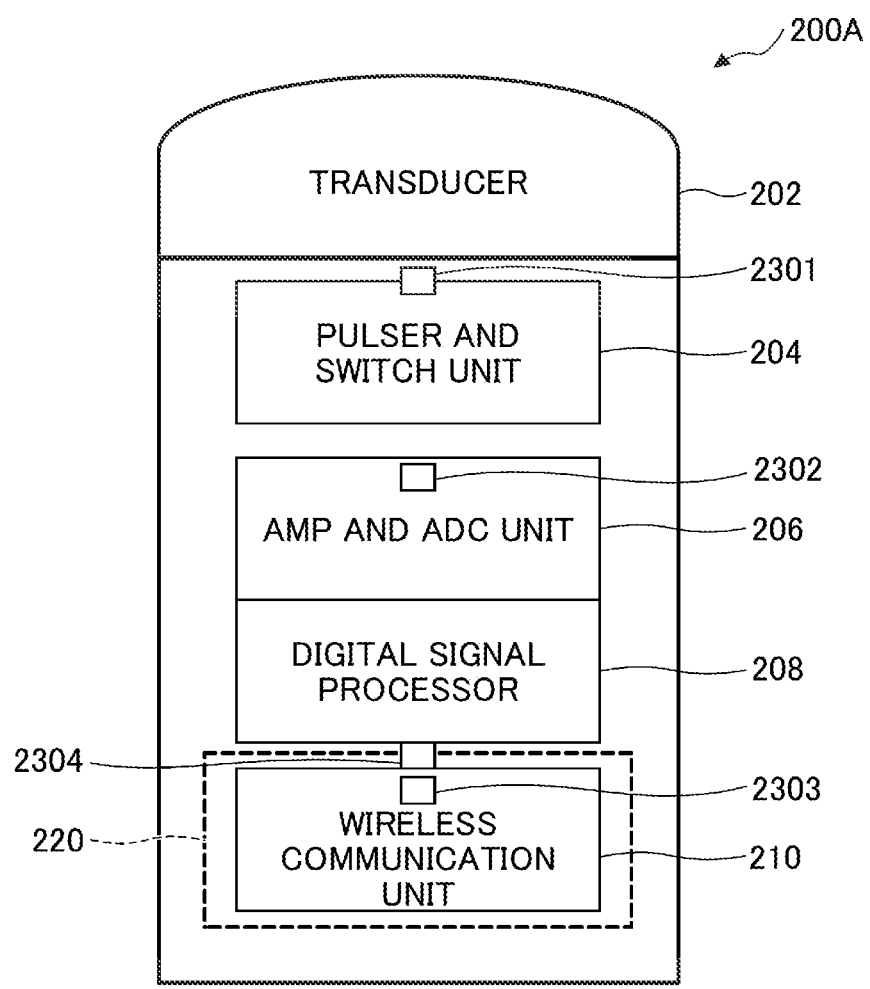
FIG. 6 depicts an overall configuration of an ultrasonic probe according to a second embodiment.

FIG. 6 depicts an overall configuration of an ultrasonic probe 200A according to a second embodiment. For elements substantially the same as those of FIG. 1, the same numerals are used, and redundant description is omitted. The ultrasonic probe 200A of the present embodiment includes a temperature sensor 2303 near or in contact with the wireless communication unit 210 and includes a temperature sensor 2304 near or in contact with the battery 220. That is, the ultrasonic probe 200A includes the four temperature sensors 230 (2301, 2302, 2303, and 2304). The other configuration of the ultrasonic probe 200A is the same as that of the ultrasonic probe 200 depicted in FIG. 1.

A circuit configuration of the ultrasonic probe 200A is substantially the same as a circuit configuration of the ultrasonic probe 200 of FIG. 3, except that the ultrasonic probe 200A additionally includes the temperature sensors 2303 and 2304. The controller 212 (see FIG. 3) of the present embodiment controls power consumption of the pulser and switch unit 204, the AMP and ADC unit 206, the wireless communication unit 210, or the battery 220, or any combination thereof based on a temperature measured by each of the temperature sensors 230. The other functions of the ultrasonic probe 200A are substantially the same as those described in FIG. 3. In addition, the ultrasonic diagnostic system 100 includes the ultrasonic probe 200A and the terminal apparatus 300.

Figure 7:
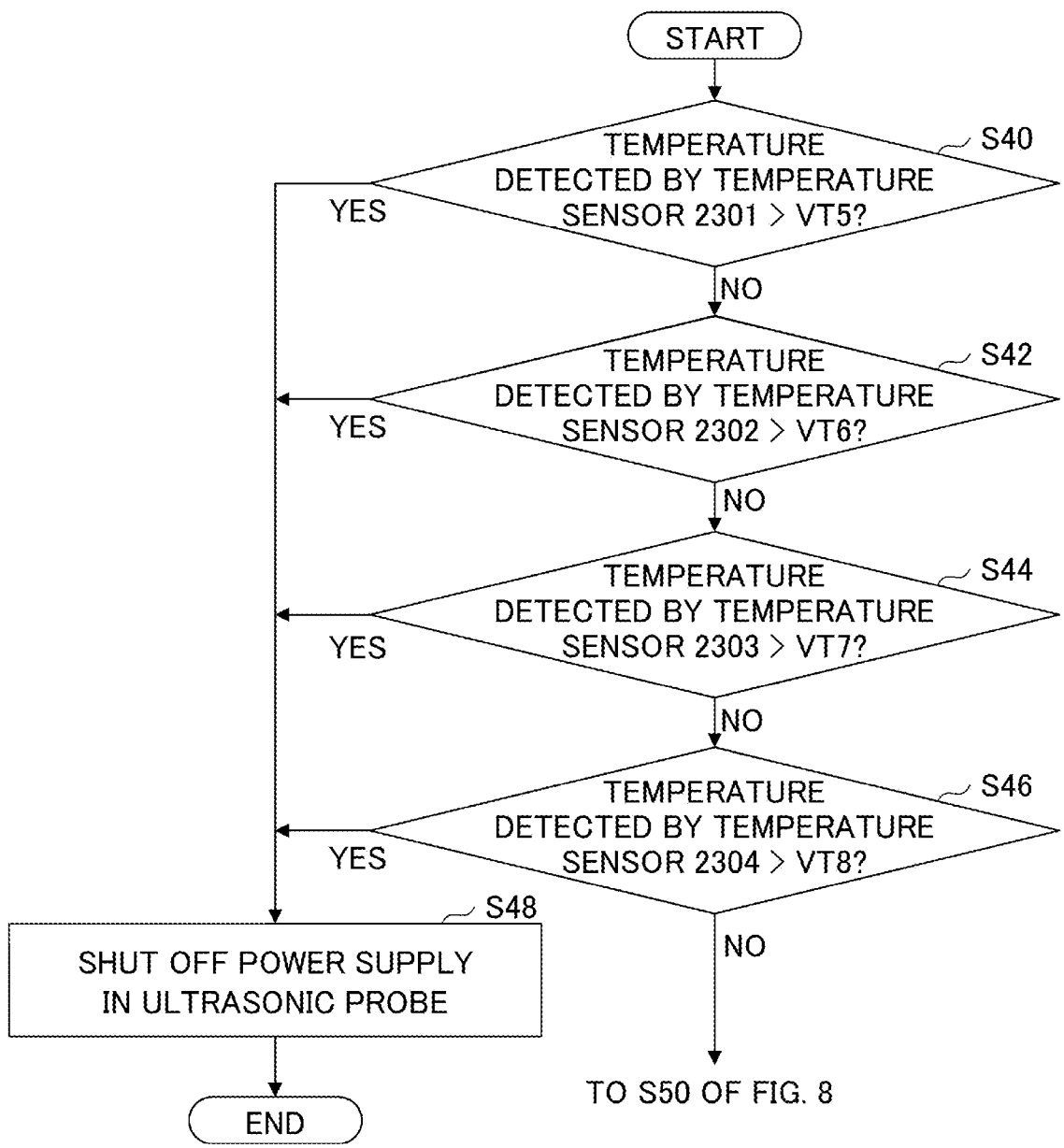
FIGS. 7-8 are diagrams depicting an example of operations of the ultrasonic probe of FIG. 6.
Figure 8:
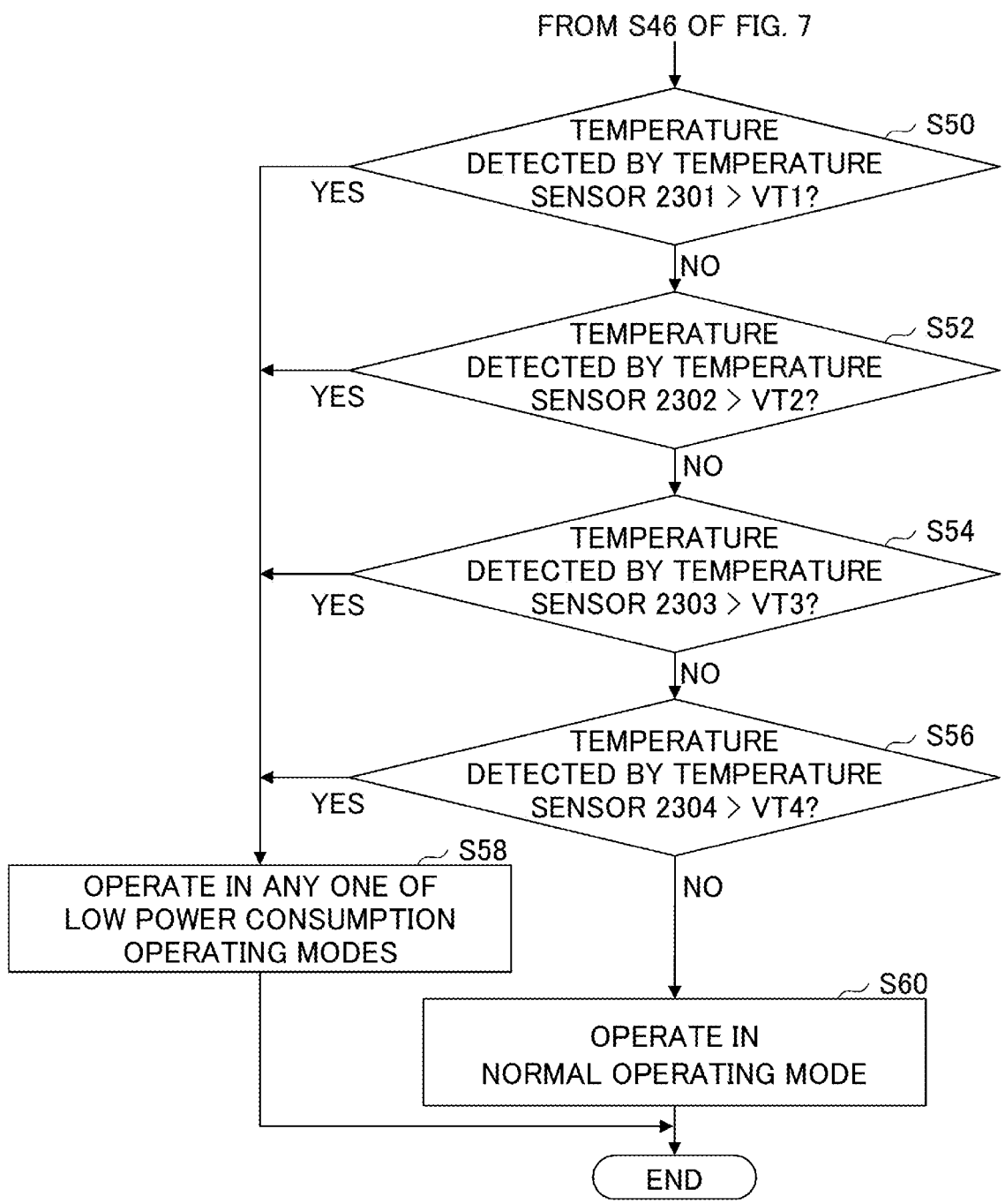

FIGS. 7 and 8 depict an example of operations of the ultrasonic probe 200A of FIG. 6. For the same operations as those of FIG. 4, redundant description is omitted. For example, an operation flow depicted in FIGS. 7 and 8 is implemented by a control program executed by the controller 212 (i.e., the CPU) of FIG. 3. That is, FIGS. 7 and 8 depict an example of a method and a control program of controlling the ultrasonic probe 200A. An operation flow depicted in FIGS. 7 and 8 is repeated at a predetermined period (e.g., every second or every 100 milliseconds) except when the power supply in the ultrasonic probe 200A is shut off.

First, in step S40, the controller 212 (FIG. 3) determines whether a temperature detected by the temperature sensor 2301 near the transducer 202 exceeds a temperature threshold VT5. When the temperature detected by the temperature sensor 2301 exceeds the temperature threshold VT5, step S48 is performed, and when the temperature detected by the temperature sensor 2301 is lower than or equal to the temperature threshold VT5, step S42 is performed.

In step S42, the controller 212 determines whether a temperature detected by the temperature sensor 2302 near the AMP and ADC unit 206 exceeds a temperature threshold VT6. When the temperature detected by the temperature sensor 2302 exceeds the temperature threshold VT6, step S48 is performed, and when the temperature detected by the temperature sensor 2302 is lower than or equal to the temperature threshold VT6, step S44 is performed.

In step S44, the controller 212 determines whether a temperature detected by the temperature sensor 2303 near the wireless communication unit 210 exceeds a temperature threshold VT7. When the temperature detected by the temperature sensor 2303 exceeds the temperature threshold VT7, step S48 is performed, and when the temperature detected by the temperature sensor 2303 is lower than or equal to the temperature threshold VT7, step S46 is performed.

In step S46, the controller 212 determines whether a temperature detected by the temperature sensor 2304 near the battery 220 exceeds a temperature threshold VT8. When the temperature detected by the temperature sensor 2304 exceeds the temperature threshold VT8, step S48 is performed, and when the temperature detected by the temperature sensor 2304 is lower than or equal to the temperature threshold VT8, step S50 of FIG. 8 is performed.

The temperature thresholds VT5-VT8 are set higher than the temperature thresholds VT1-VT4 described with reference to FIG. 8, respectively. The temperature thresholds VT5-VT8 are the upper limit temperatures for stable operations of corresponding ones of the various components provided in the ultrasonic probe 200A. The temperature thresholds VT5-VT8 may be set to have the same value as each other, or may be set to have values corresponding to amounts of heat generation of respective components. The temperature thresholds VT5-VT8 are an example of second temperature thresholds.

In step S48, the controller 212 shuts off the power supply in the ultrasonic probe 200A, for example, by stopping the power output from the battery 220. This stops operation of the ultrasonic probe 200A. If any of the temperatures measured by the plurality of temperature sensors 230 exceeds a corresponding one of the temperature thresholds VT5-VT8, the power supply in the ultrasonic probe 200A can be shut off to prevent a corresponding one of the various components from breaking down due to heat generation.

Steps S50 and S52 of FIG. 8 are similar steps S10 and S12 of FIG. 4. In step S50, when a temperature detected by the temperature sensor 2301 exceeds the temperature threshold VT1, the controller 212 performs step S58, and when the temperature detected by the temperature sensor 2301 is lower than or equal to the temperature threshold VT1, the controller 212 performs step S52. In step S52, when a temperature detected by the temperature sensor 2302 exceeds the temperature threshold VT2, the controller 212 performs step S58, and when the temperature detected by the temperature sensor 2302 is lower than or equal to the temperature threshold VT2, the controller 212 performs step S54.

In step S54, the controller 212 determines whether a temperature detected by the temperature sensor 2303 near the wireless communication unit 210 exceeds the temperature threshold VT3. When the temperature detected by the temperature sensor 2303 exceeds the temperature threshold VT3, the controller 212 performs step S58, and when the temperature detected by the temperature sensor 2303 is lower than or equal to the temperature threshold VT3, the controller 212 performs step S56.

In step S56, the controller 212 determines whether a temperature detected by the temperature sensor 2304 near the battery 220 exceeds the temperature threshold VT4. When the temperature detected by the temperature sensor 2304 exceeds the temperature threshold VT4, the controller 212 performs step S58, and when the temperature detected by the temperature sensor 2304 is lower than or equal to the temperature threshold VT4, the controller 212 performs step S60.

The temperature thresholds VT1-VT4 may be set to the values same as each other or values different from each other. For example, as in the first embodiment, the temperature threshold VT1 may be set lower than each of the other temperature thresholds VT2, VT3, and VT4.

In step S58, the controller 212 switches an operating mode of the ultrasonic probe 200A to one of a plurality of low power consumption operating modes because any one of the temperatures measured by the four temperature sensors 230 exceeds the temperature threshold set for the corresponding one of the temperature sensors 230. In step S60, the controller 212 maintains an operating mode of the ultrasonic probe 200A as being a normal operating mode or switches an operating mode of the ultrasonic probe 200A to the normal operating mode.

Figure 9:
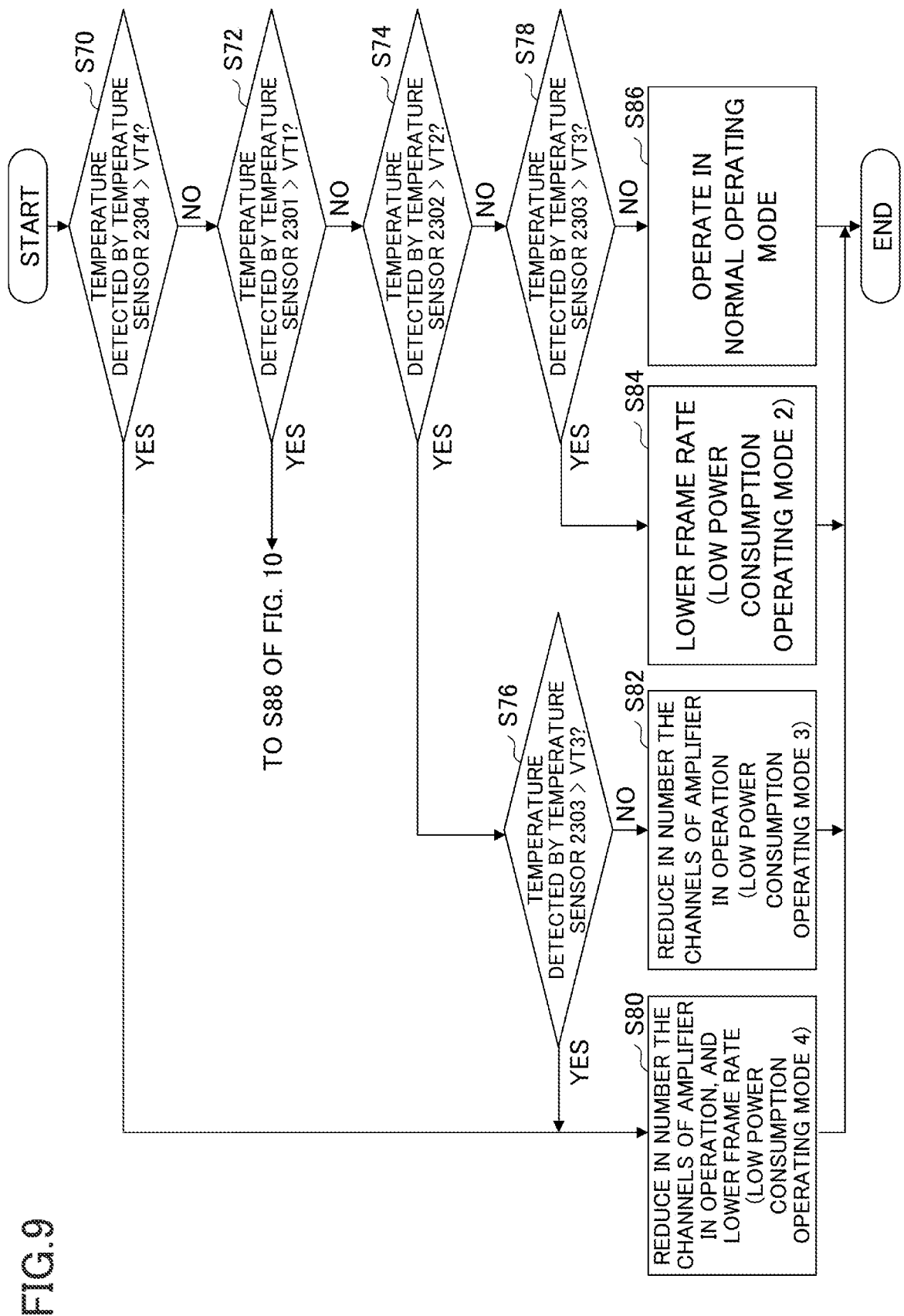
FIGS. 9-10 are diagrams depicting a specific example of the operations depicted in FIG. 8.
Figure 10:
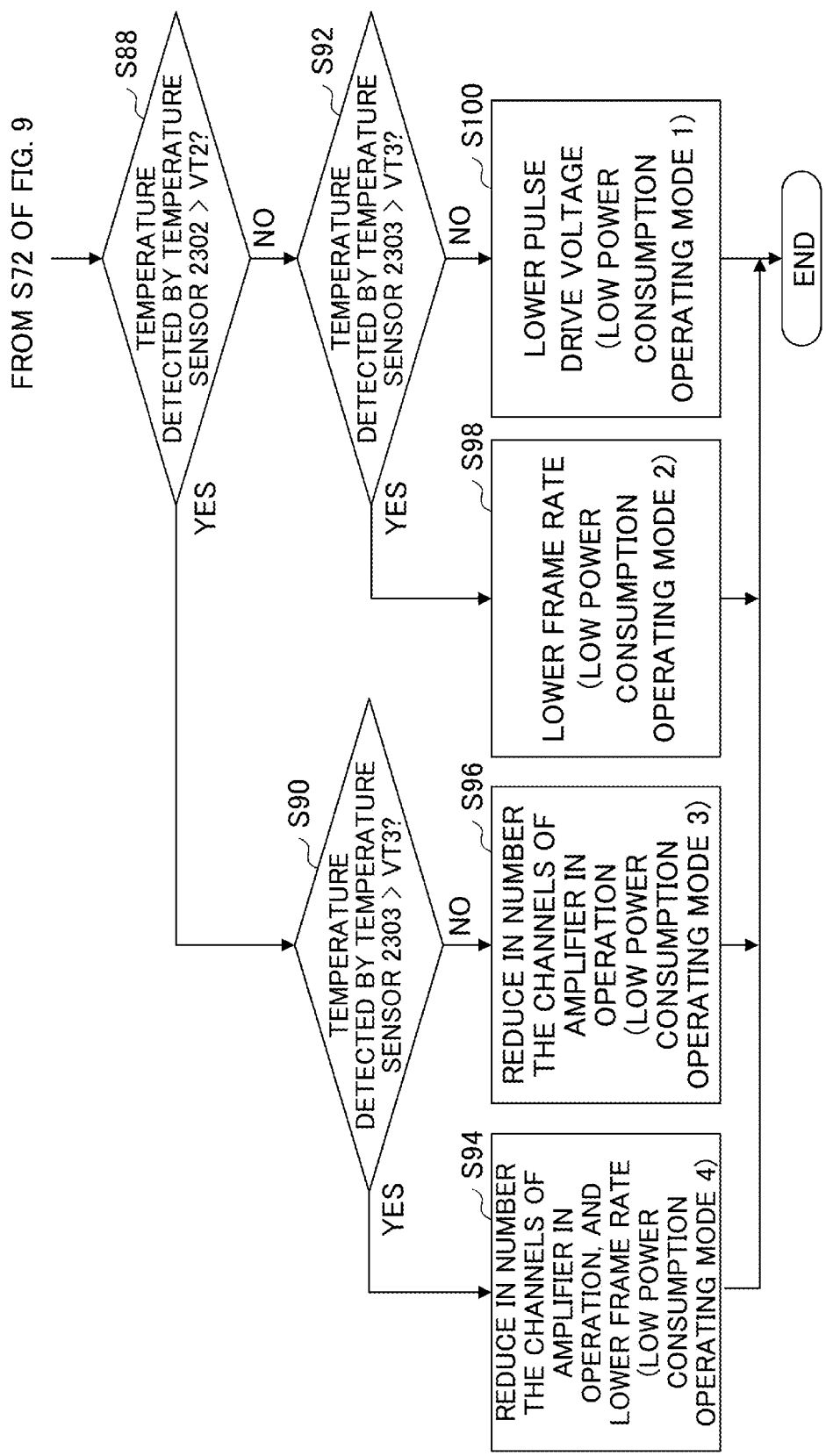

FIGS. 9 and 10 depict a specific example of the operations depicted in FIG. 8. A determination of step S70 is the same as a determination of step S56 of FIG. 8, and a determination of step S72 is the same as a determination of step S50 of FIG. 8. A determination of step S74 is the same as a determination of step S52 in FIG. 8, and each of determinations of steps S76 and S78 is the same as a determination of step S54 in FIG. 8.

In step S70, when the ambient temperature of the battery 220 measured by the temperature sensor 2304 exceeds the temperature threshold VT4, the controller 212 performs step S80 regardless of the temperatures measured by the other temperature sensors 2301 through 2303. In step S70, the controller 212 performs step S72 when the temperature measured by the temperature sensor 2304 is lower than or equal to the temperature threshold VT4.

In step S72, the controller 212 performs step S88 of FIG. 10 when the ambient temperature of the transducer 202 and the pulser and switch unit 204 measured by the temperature sensor 2301 exceeds the temperature threshold VT1. In step S72, the controller 212 performs step S74 when the ambient temperature of the transducer 202 and the pulser and switch unit 204 measured by the temperature sensor 2301 is lower than or equal to the temperature threshold VT1.

In step S74, when the ambient temperature of the AMP and ADC unit 206 measured by the temperature sensor 2302 exceeds the temperature threshold VT2, the controller 212 performs step S76, and when the temperature measured by the temperature sensor 2302 is lower than or equal to the temperature threshold VT2, the controller 212 performs step S74.

In step S76, when the ambient temperature of the wireless communication unit 210 measured by the temperature sensor 2303 exceeds the temperature threshold VT3, the controller 212 performs step S80. In step S76, when the temperature measured by the temperature sensor 2303 is lower than or equal to the temperature threshold VT3, the controller 212 performs step S82.

In step S78, when the temperature measured by the temperature sensor 2303 exceeds the temperature threshold VT3, the controller 212 performs step S84. In step S78, when the temperature measured by the temperature sensor 2303 is lower than or equal to the temperature threshold VT3, the controller 212 performs step S86.

In step S80, the controller 212 reduces in number the channels of the amplifier of the AMP and ADC unit 206 in operation and lowers a frame rate of ultrasonic image data to be transmitted to the wireless communication unit 302 of the terminal apparatus 300 by the wireless communication unit 210 (i.e., a low power consumption operating mode 4). As a result, power consumption of the AMP and ADC unit 206 and the wireless communication unit 210 can be reduced, and ambient temperatures of the AMP and ADC unit 206 and the wireless communication unit 210 can be lowered.

When a frame rate is thus lowered, also a frequency of transmissions of ultrasonic waves by the transducer 202 is reduced. In this case, a frequency of pulse generation and a frequency of operations of the switches in the pulser and switch unit 204, a frequency of operations of the amplifier and the ADC in the AMP and ADC unit 206, and a frequency of ultrasonic image data generation in the digital signal processor 208 are reduced.

Therefore, power consumption of the pulser and switch unit 204, the AMP and ADC unit 206, and the digital signal processor 208 as well as power consumption of the wireless communication unit 210 can be reduced. At this time, power consumption of the AMP and ADC unit 206 can be reduced through both the reduction in number of the channels in operation and the decrease in a frequency of operations. Therefore, ambient temperatures of the pulser and switch unit 204, the AMP and ADC unit 206, the digital signal processor 208, and the wireless communication unit 210 can be lowered.

In step S82, the controller 212 reduces in number the channels of the amplifier of the AMP and ADC unit 206 in operation (i.e., a low power consumption operating mode 3).

In step S84, the controller 212 lowers a frame rate of ultrasonic image data to be transmitted to the wireless communication unit 302 by the wireless communication unit 210 (i.e., a low power consumption operating mode 2). As described above, by lowering a frame rate, not only power consumption of the wireless communication unit 210 but also power consumption of the pulser and switch unit 204, the AMP and ADC unit 206, and the digital signal processor 208 can be reduced. Accordingly, in step S84, ambient temperatures of the pulser and switch unit 204, the AMP and ADC unit 206, the digital signal processor 208, and the wireless communication unit 210 can be lowered.

In step S86, as in step S32 of FIG. 5, the controller 212 causes the ultrasonic probe 200A to operate in the normal operating mode and controls an operation of a circuit in each element of the ultrasonic probe 200A according to the normal operating mode.

In step S88 of FIG. 10, when the ambient temperature of the AMP and ADC unit 206 measured by the temperature sensor 2302 exceeds the temperature threshold VT2, the controller 212 performs step S90. In step S88, the controller 212 performs step S92 when the temperature measured by the temperature sensor 2302 is lower than or equal to the temperature threshold VT2.

In step S90, when the ambient temperature of the wireless communication unit 210 measured by the temperature sensor 2303 exceeds the temperature threshold VT3, the controller 212 performs step S94.

In step S90, when the temperature measured by the temperature sensor 2303 is lower than or equal to the temperature threshold VT3, the controller 212 performs step S96.

In step S92, when the temperature measured by the temperature sensor 2303 exceeds the temperature threshold VT3, the controller 212 performs step S98. In step S92, when the temperature measured by the temperature sensor 2303 is lower than or equal to the temperature threshold VT3, the controller 212 performs step S100.

Step S94 is the same as step S80 in FIG. 9 (i.e., a low power consumption operating mode 4). Step S96 is the same as step S82 in FIG. 9 (i.e., a low power consumption operating mode 3). Step S98 is the same as step S84 in FIG. 9 (i.e., a low power consumption operating mode 2).

In step S100, as in step S28 of FIG. 5, the controller 212 controls the pulser voltage generating unit 214 to reduce drive voltages in the pulser and switch unit 204 (i.e., a low power consumption operating mode 1). As a result, power consumption of the pulser and switch unit 204 can be reduced, also heat generation of the transducer 202 can be reduced, and thus, an ambient temperature of the pulser and switch unit 204 and an ambient temperature of the transducer 202 can be lowered.

Figure 11:
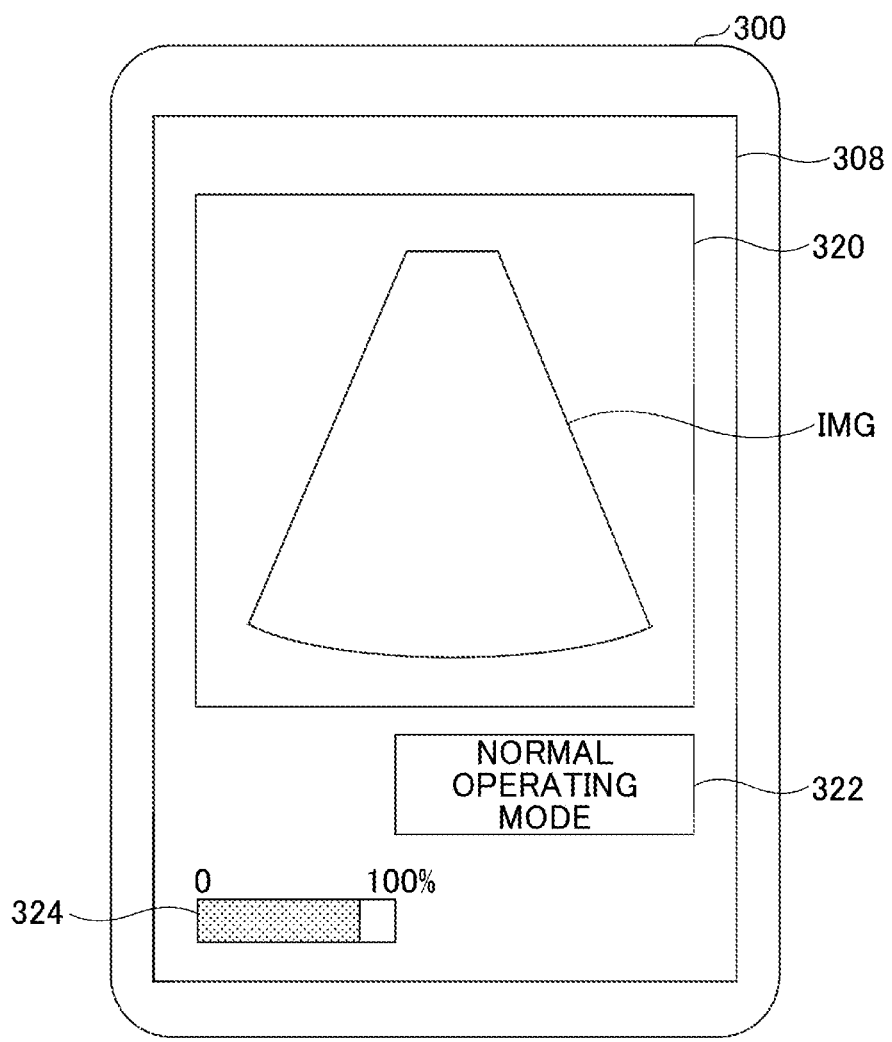
FIG. 11 is a diagram depicting an example of an ultrasonic image displayed on a screen of a terminal apparatus depicted in FIG. 3.

FIG. 11 depicts an example of an ultrasonic image IMG displayed on the display unit 308 of the terminal apparatus 300 of FIG. 3. For example, in FIG. 11, the terminal apparatus 300 is a tablet terminal. The ultrasonic image IMG with respect to a subject generated by the digital signal processor 208 of the ultrasonic probe 200A is displayed in an image window 320 on the display unit 308. For example, the display unit 308 may be a liquid crystal display or an organic electroluminescence (EL) display.

For example, in a display window 322 for an operating mode on the display unit 308, a character string indicating a current operating mode, i.e., "NORMAL OPERATING MODE" is displayed. For example, in response to a transition of the ultrasonic probe 200A to a low power consumption operating mode, the display window 322 displays a character string indicating "LOW POWER CONSUMPTION OPERATING MODE 1", "LOW POWER CONSUMPTION OPERATING MODE 2", "LOW POWER CONSUMPTION OPERATING MODE 3", or "LOW POWER CONSUMPTION OPERATING MODE 4" according to the current operating mode. Note that the display window 322 may display a number, a symbol, an image, or the like indicating a specific one of the low power consumption operating modes.

An indicator window 324 on the display unit 308 displays remaining power of the battery 220. In the example of FIG. 11, the remaining power of the battery 220 is displayed as about 80%.

As described above, in the second embodiment, the same advantageous effects as those of the first embodiment can be obtained. For example, power consumption of a component near a temperature sensor 230 that detects a temperature exceeding a corresponding one of the temperature thresholds VT1-VT4 can be reduced to reduce heat generation. As a result, it is possible to cause a surface temperature of the casing of the ultrasonic probe 200A at a position that differs depending on a position of a heat generating component to be lower than or equal to a corresponding one of the temperature thresholds VT1-VT4, and it is possible to prevent both a subject and an operator of the ultrasonic probe 200A from feeling discomfort.

Further, in the second embodiment, when any one of temperatures measured by the plurality of temperature sensors 230 exceeds a corresponding one of the temperature thresholds VT5-VT8, the power supply in the ultrasonic probe 200A can be shut off to prevent a corresponding one of the various components from breaking down due to heat generation.

In addition, it is possible to reduce power consumption of components near corresponding ones of the temperature sensors 230 detecting temperatures exceeding the temperature thresholds VT3 and VT4, thereby reducing amounts of heat generation accordingly. Thus, when measured temperatures of plural ones of the temperature sensors 230 exceed respective temperature thresholds (corresponding two or more of the temperature thresholds VT1-VT4), power consumption of the corresponding plurality of components can be adjusted by reducing power consumption of these plurality of components. As a result, a surface temperature of the casing of the ultrasonic probe 200A at corresponding positions can be set to desired temperatures, while minimizing degradation in quality of an ultrasonic image, for example.

When a measured temperature of the temperature sensor 2304 near the battery that supplies the power to all the circuits exceeds the temperature threshold VT4, power consumption of the plurality of components can be overall reduced, thereby reducing heat generation of each component equally while reducing heat generation of the battery 220.

Third Embodiment

Figure 12:
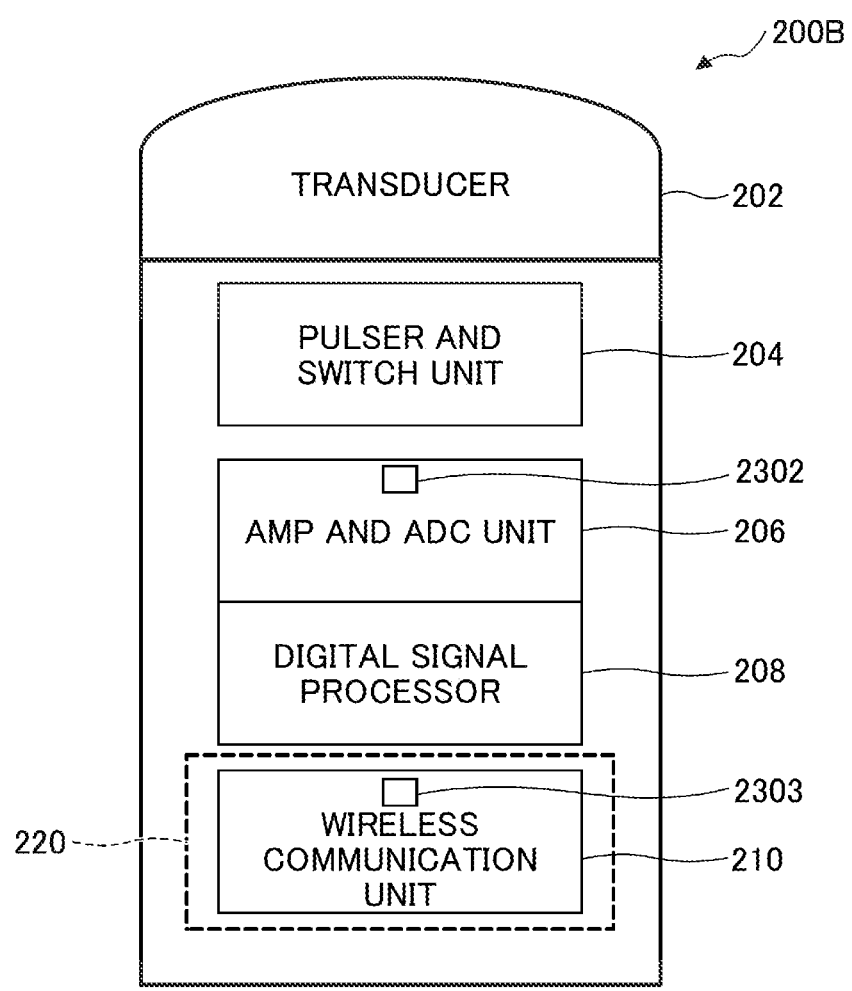
FIG. 12 depicts an overall configuration of an ultrasonic probe according to a third embodiment.

FIG. 12 depicts an overall configuration of an ultrasonic probe 200B according to a third embodiment. For elements substantially the same as those of FIG. 1, the same numerals are used, and redundant description is omitted. The ultrasonic probe 200B of the present embodiment includes the temperature sensor 2302 near or in contact with the amplifier in the AMP and ADC unit 206 and includes the temperature sensor 2303 near or in contact with the wireless communication unit 210. The temperature sensor 2301 near the pulser and switch unit 204 is not provided. The other configuration of the ultrasonic probe 200B is the same as that of the ultrasonic probe 200 depicted in FIG. 1.

For example, an arrangement of the temperature sensors 2302 and 2303 depicted in FIG. 12 is one example of an arrangement of temperature sensors for the ultrasonic probe 200B for which it is known that a temperature at the tip of the transducer 202 will not increase to the extent that a subject feels uncomfortable. If a capacity of the battery 220 is large and heat generation of the battery 220 is large, the temperature sensor 2304 depicted in FIG. 6 may be provided near or in contact with the battery 220.

A circuit configuration of the ultrasonic probe 200B is substantially the same as a circuit configuration modified from the circuit configuration of FIG. 3 in that the temperature sensor 2303 is provided instead of the temperature sensor 2301. The ultrasonic probe 200B and the terminal apparatus 300 are included in the ultrasonic diagnostic system 100. The controller 212 (FIG. 3) of the present embodiment controls a temperature of each element of the ultrasonic probe 200B (i.e., controls corresponding power consumption) by performing steps S74, S76, S78, S80, S82, S84, and S86 of FIG. 9. Control of temperatures of the elements of the ultrasonic probe 200B is implemented as a result of the controller 212 (i.e., the CPU) executing a control program.

Also the third embodiment can obtain the same advantageous effects as those of the first embodiment. For example, by providing temperature sensors 230 near elements having larger amounts of heat generation than other elements, a surface temperature of the casing of the ultrasonic probe 200B at each position can be set to a desired temperature.

Fourth Embodiment

Figure 13:
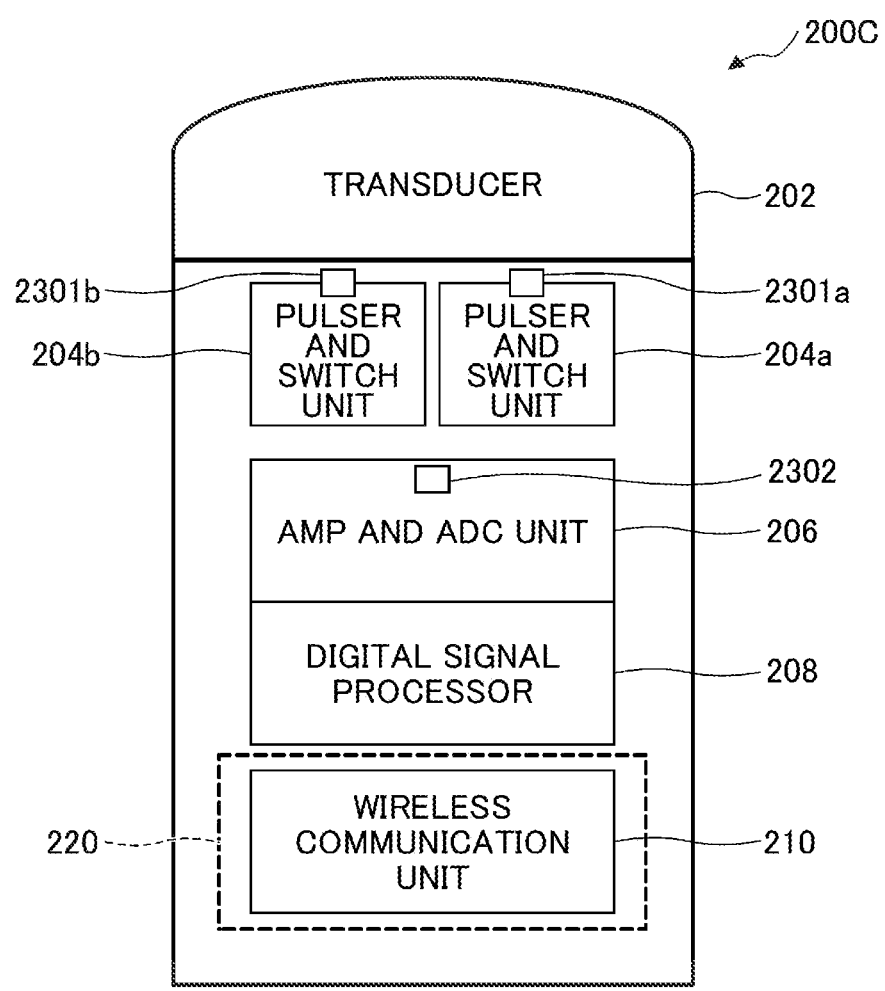
FIG. 13 depicts an overall configuration of an ultrasonic probe according to a fourth embodiment.

FIG. 13 depicts an overall configuration of an ultrasonic probe 200C according to a fourth embodiment. For elements substantially the same as those of FIG. 1, the same numerals are used, and redundant description is omitted. The ultrasonic probe 200C in the present embodiment includes two pulser and switch units 204 (204a and 204b) and two temperature sensors 2301 (2301a and 2301b) corresponding to the respective pulser and switch units 204. In the ultrasonic probe 200C, the configuration except for the pulser and switch units 204 and the temperature sensors 2301 is the same as that of the ultrasonic probe 200 depicted in FIG. 1. Each of the temperature sensors 2301 detects an ambient temperature of a corresponding one of the pulser and switch units 204 and an ambient temperature of the transducer 202.

In the case where the ultrasonic probe 200C thus includes the two pulser and switch units 204a and 204b, the temperature sensors 2301a and 2301b are thus provided corresponding to the respective pulser and switch units 204 to control amounts of heat generation at corresponding positions of the ultrasonic probe 200C more finely. This prevents an operator who holds and operates the ultrasonic probe 200C from feeling discomfort with respect to a surface temperature of the casing of the ultrasonic probe 200C.

A circuit configuration of the ultrasonic probe 200C is substantially the same as that of the ultrasonic probe 200 depicted in FIG. 3, except that the single pulser and switch unit 204 is used in the ultrasonic probe 200 whereas the plurality of pulser and switch units 204 (i.e., the plurality of divisions obtained from the pulser and switch unit 204 of FIG. 3 being divided) are used in the ultrasonic probe 200C; and the single temperature sensor 2301 is used in the ultrasonic probe 200 whereas the two temperature sensors 2301 are used in the ultrasonic probe 200C. The ultrasonic probe 200C and the terminal apparatus 300 are included in the ultrasonic diagnostic system 100.

A manner of controlling temperatures (i.e., controlling power consumption) at various positions of the ultrasonic probe 200C by the controller 212 (see FIG. 3) in the present embodiment is substantially the same as that of FIG. 5. However, according to the present embodiment, in step S20 of FIG. 5, when any of the plurality of pulser and switch units 204 detects a temperature exceeding the temperature threshold VT1, for example, step S22 is performed. When all of the plurality of pulser and switch unit 204 detect temperatures, each of which is lower than or equal to the temperature threshold VT1, step S24 is performed. Controlling temperatures at the various positions of the ultrasonic probe 200C is implemented by the controller 212 (i.e., the CPU) executing a control program.

In a case where the capacity of the battery 220 is large and heat generation of the battery 220 is large, the temperature sensor 2304 depicted in FIG. 6 may be provided near or in contact with the battery 220. When an amount of heat generation of the wireless communication unit 210 is large, the temperature sensor 2303 depicted in FIG. 6 may be provided near or in contact with the wireless communication unit 210. In this case, operations substantially the same as those depicted in FIGS. 9 and 10 are performed. In addition, when another unit, such as an AMP and ADC unit 206, includes a plurality of parts, i.e., when a plurality of AMP and ADC units 206 are provided in the ultrasonic probe, a temperature sensor may be individually provided for each of these parts or units.

The fourth embodiment can obtain the same advantageous effects as those of the first embodiment. In addition, according to the fourth embodiment, in the case where the ultrasonic probe 200C includes the plurality of pulser and switch units 204, the temperature sensor 2301 may be individually provided for each of the pulser and switch units 204 to control amounts of heat generation at corresponding positions of the ultrasonic probe 200C more finely.

Fifth Embodiment

Figure 14:
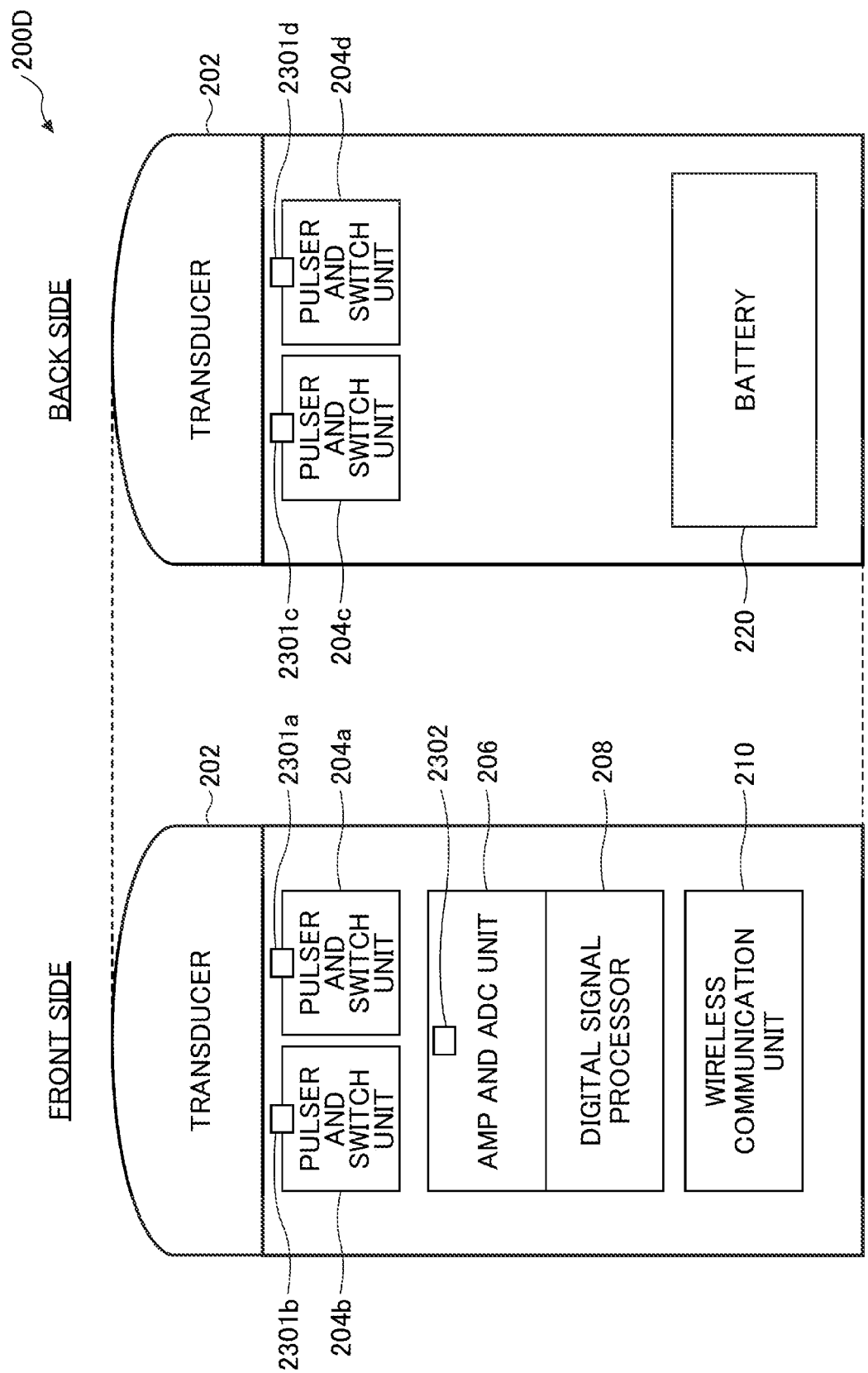
FIG. 14 depicts an overall configuration of an ultrasonic probe according to a fifth embodiment.

FIG. 14 depicts an overall configuration of an ultrasonic probe 200D according to a fifth embodiment. For elements substantially the same as those of FIGS. 1 and 13, the same numerals are used, and redundant description is omitted. The ultrasonic probe 200D in the present embodiment includes four pulser and switch units 204 (204a, 204b, 204c, and 204d), and four temperature sensors 2301 (2301a, 2301b, 2301c, and 2301d) corresponding to the respective pulser and switch units 204.

The pulser and switch units 204a and 204b and the temperature sensors 2301a and 2301b are provided at a front side in the ultrasonic probe 200D. The pulser and switch units 204c and 204d and the temperature sensors 2301c and 2301d are provided at a back side in the ultrasonic probe 200D. In the ultrasonic probe 200D, a configuration except for the pulser and switch units 204 and the temperature sensors 2301 is the same as that of the ultrasonic probe 200 depicted in FIG. 1. Each of the temperature sensors 2301 detects an ambient temperature of a corresponding one of the pulser and switch units 204 and an ambient temperature of the transducer 202.

As in the embodiment of FIG. 13, in the case where the ultrasonic probe 200D thus includes the plurality of pulser and switch units 204, it is possible to more finely control the amounts of heat generation at corresponding positions of the ultrasonic probe 200D, by providing the temperature sensors 2301 corresponding to the respective pulser and switch units 204. This prevents an operator who holds and operates the ultrasonic probe 200D from feeling discomfort with respect to a surface temperature of the casing of the ultrasonic probe 200D.

A circuit configuration of the ultrasonic probe 200D is substantially the same as that of the ultrasonic probe 200 depicted in FIG. 3, except that the single pulser and switch unit 204 is used in the ultrasonic probe 200 of FIG. 3 whereas the plurality of pulser and switch units 204 (i.e., a plurality of divisions obtained from the pulser and switch unit 204 of FIG. 3 being divided) and the plurality of temperature sensors 2301 are used in the ultrasonic probe 200D. The ultrasonic probe 200D and the terminal apparatus 300 are included in the ultrasonic diagnostic system 100.

A manner of controlling temperatures (i.e., controlling power consumption) at various positions of the ultrasonic probe 200D by the controller 212 (see FIG. 3) of the present embodiment is the same as that of the embodiment of FIG. 5. As having been described with reference to FIG. 13, according to the present embodiment, in step S20 of FIG. 5, for example, when one of the plurality of pulser and switch units 204 detects a temperature exceeding the temperature threshold VT1, step S22 is performed. When all of the plurality of pulser and switch units 204 detect temperatures, each of which is lower than or equal to the temperature threshold VT1, step S24 is performed. Controlling temperatures at various positions of the ultrasonic probe 200D is implemented by the controller 212 (i.e., the CPU) executing a control program.

Also in the fifth embodiment, the same advantageous effects as those of the first embodiment and the fourth embodiment can be obtained.

All examples and conditional language recited herein are intended for pedagogical purposes to aid the reader in understanding the invention and the concepts contributed by the inventors to furthering the art, and are to be construed as being without limitation to such specifically recited examples and conditions, nor does the organization of such examples in the specification relate to a showing of the superiority and inferiority of the invention. Although the ultrasonic probes, ultrasonic diagnostic systems, methods of controlling an ultrasonic probes, and non-transitory computer-readable recording mediums have been described with reference to the embodiments, it should be understood that the invention is not limited to these embodiments, and the various changes, substitutions, and alterations could be made hereto without departing from the spirit and scope of the invention.

What is claimed is:

1. An ultrasonic probe, comprising:
    a transducer configured to transmit an ultrasonic wave to a subject and output a signal generated based on an ultrasonic wave reflected by the subject;
    a pulser configured to output a pulse signal to the transducer and output a signal that is based on the signal output by the transducer;
    an amplifier configured to amplify the signal that is output by the pulser and is based on the signal output by the transducer;
    a wireless transmitter configured to receive data obtained from a signal that has been amplified by the amplifier and transmit the data to outside;
    a first temperature detector provided at a position near or in contact with the pulser, and a second temperature detector provided at a position near or in contact with the amplifier; and
    a processor configured to:
        compare a temperature detected by the first temperature detector with a first threshold, and when the temperature detected by the first temperature detector exceeds the first temperature threshold, switch an operating mode of the pulser from a normal operating mode to a low power consumption operating mode in which power consumption is lower than power consumption in the normal operating mode, and
        compare a temperature detected by the second temperature detector with a second threshold, and when the temperature detected by the second temperature detector exceeds the second temperature threshold, switch an operating mode of the amplifier from a normal operating mode to a low power consumption operating mode in which power consumption is lower than power consumption in the normal operating mode.

2. The ultrasonic probe as claimed in claim 1, wherein the processor is further configured to shut off power supply in the ultrasonic probe when the temperature detected by the first temperature detector or the temperature detected by the second temperature detector exceeds a third temperature threshold that is higher than the first temperature threshold and the second temperature threshold.

3. The ultrasonic probe as claimed in claim 1, wherein:
    the amplifier has a plurality of channels, and
    the processor is further configured to, in the low power consumption operating mode of the amplifier, reduce in number the channels of the amplifier in operation.

4. The ultrasonic probe according to claim 1, further comprising a voltage generator configured to generate a drive voltage with respect to the pulser,
    wherein the processor is further configured to, in the low power consumption operating mode of the pulser, lower the drive voltage generated by the voltage generator.

5. The ultrasonic probe as claimed in claim 1, further comprising a third temperature detector provided at a position near or in contact with the wireless transmitter,
    wherein the processor is further configured to compare a temperature detected by the third temperature detector with a fourth temperature threshold, the processor being further configured to, when the temperature detected by the third temperature detector exceeds the fourth temperature threshold, lower a frequency of signal transmissions from the wireless transmitter to outside.

6. The ultrasonic probe as claimed in claim 1, further comprising:
- a battery configured to supply power to at least the pulser, the amplifier, the wireless transmitter, and the processor; and
- a fourth temperature detector provided at position near or in contact with the battery,
- wherein the processor is further configured to reduce in number the channels of the amplifier in operation and reduce a frequency of signal transmissions from the wireless transmitter to outside when a temperature detected by the fourth temperature detector exceeds a fifth temperature threshold.

7. The ultrasonic probe as claimed in claim 1, wherein the first temperature thresholds is set to a temperature lower than the second temperature threshold.

8. An ultrasonic diagnostic system comprising:
an ultrasonic probe; and
a terminal apparatus configured to display an ultrasonic image obtained by the ultrasonic probe,
wherein the ultrasonic probe includes:
- a transducer configured to transmit an ultrasonic wave to a subject and output a signal generated based on an ultrasonic wave reflected by the subject;
- a pulser configured to output a pulse signal to the transducer and output a signal that is based on the signal output by the transducer;
- an amplifier configured to amplify the signal that is output by the pulser and is based on the signal output by the transducer;
- a wireless transmitter configured to receive data obtained from a signal that has been amplified by the amplifier and transmit the data to outside;
- a first temperature detector provided at a position near or in contact with the pulser, and a second temperature detector provided at a position near or in contact with the amplifier; and
- a processor configured to:
  - compare a temperature detected by the first temperature detector with a first threshold, and when the temperature detected by the first temperature detector exceeds the first temperature threshold, switch an operating mode of the pulser from a normal operating mode to a low power consumption operating mode in which power consumption is lower than power consumption in the normal operating mode, and
  - compare a temperature detected by the second temperature detector with a second threshold, and when the temperature detected by the second temperature detector exceeds the second temperature threshold, switch an operating mode of the amplifier from a normal operating mode to a low power consumption operating mode in which power consumption is lower than power consumption in the normal operating mode.

9. The ultrasonic diagnostic system as claimed in claim 8, wherein
the terminal apparatus includes a display configured to display the ultrasonic image and indicate a least one of the low power consumption operating mode of the pulser or the low power consumption operating mode of the amplifier, when the ultrasonic probe is set in the a least one of the low power consumption operating mode of the pulser or the low power consumption operating mode of the amplifier.

10. A method of controlling an ultrasonic probe that includes a transducer configured to transmit an ultrasonic wave to a subject and output a signal generated based on an ultrasonic wave reflected by the subject; a pulser configured to output a pulse signal to the transducer and output a signal that is based on the signal output by the transducer; an amplifier configured to amplify the signal that is output by the pulser and is based on the signal output by the transducer; a wireless transmitter configured to receive data obtained from a signal that has been amplified by the amplifier and transmit the data to outside; and a processor, the method comprising:
- detecting a first temperature by a first temperature detector provided at a position near or in contact with the pulser;
- detecting a second temperature by a second temperature detector provided at a position near or in contact with the amplifier;
- comparing the first temperature with a first threshold, and when the first temperature exceeds the first temperature threshold, switching an operating mode of the pulser from a normal operating mode to a low power consumption operating mode in which power consumption is lower than power consumption in the normal operating mode; and
- comparing the second temperature with a second threshold, and when the second temperature exceeds the second temperature threshold, switching an operating mode of the amplifier from a normal operating mode to a low power consumption operating mode in which power consumption is lower than power consumption in the normal operating mode.

11. A non-transitory computer-readable recording medium storing a control program,
wherein, when executed by the processor, the control program causes the processor to perform the method of claim 10.

* * * * *